United States Patent [19]

Wardlaw et al.

[11] Patent Number: 4,808,379
[45] Date of Patent: * Feb. 28, 1989

[54] DEVICE FOR OBTAINING STOOL SAMPLES AND DETECTING OCCULT BLOOD

[76] Inventors: Stephen C. Wardlaw, 128 Sunset Hill Dr., Branford, Conn. 06405; Robert A. Levine, 31 Pilgrim La., Guilford, Conn. 06437

[*] Notice: The portion of the term of this patent subsequent to Feb. 14, 2006 has been disclaimed.

[21] Appl. No.: 699,748

[22] Filed: Feb. 8, 1985

[51] Int. Cl.⁴ .................... G01N 21/78; G01N 33/72
[52] U.S. Cl. ...................................... 422/56; 128/638; 128/759; 422/58; 422/61; 436/66; 435/28; 435/805
[58] Field of Search .................. 422/56, 57, 58, 61; 436/66, 169, 170; 128/638, 749, 356, 759; 435/28, 845

[56] References Cited

U.S. PATENT DOCUMENTS

| | | | |
|---|---|---|---|
| 3,996,006 | 12/1976 | Pagano | 23/253 |
| 4,175,923 | 11/1979 | Friend | 422/56 X |
| 4,225,557 | 9/1980 | Hartl et al. | 422/56 |
| 4,259,964 | 4/1981 | Levine | 128/638 |
| 4,273,741 | 6/1981 | Levine | 128/638 X |
| 4,328,184 | 5/1982 | Kondo | 422/58 |
| 4,365,970 | 12/1982 | Lawrence et al. | 436/66 |
| 4,367,750 | 1/1983 | Levine | 128/759 X |
| 4,420,353 | 12/1983 | Levine | 128/638 X |
| 4,486,536 | 12/1984 | Baker et al. | 422/58 X |
| 4,541,987 | 9/1985 | Guadagno | 436/66 X |
| 4,559,949 | 12/1985 | Levine | 436/66 X |

FOREIGN PATENT DOCUMENTS 0124214 11/1984 European Pat. Off. .
0124215 11/1984 European Pat. Off. .
2031583 4/1980 United Kingdom .

Primary Examiner—Barry S. Richman
Assistant Examiner—Robert J. Hill, Jr.
Attorney, Agent, or Firm—Price, Heneveld, Cooper, DeWitt & Litton

[57] ABSTRACT

The device is used in the same way as toilet tissue to obtain a stool sample for occult blood testing on a receptor sheet included in the device. The receptor sheet is preimpregnated with guaiac or other suitable reagent. A performance/control monitor is included in the device and is kept separated and spaced apart from the receptor sheet until after the stool sample is obtained. Once the stool sample is obtained, the performance/control monitor is brought into and retained in face-to-face contact with the receptor sheet. Upon return to the physician, the developer reagent is applied to the receptor sheet in the area of the stool and in the area of the monitor. Maintaining the monitor out of contact with the receptor sheet until the stool sample is taken prevents the occurrence of a false positive monitor reaction, which can happen when there is extended contact between the monitor and the reagent impregnated receptor sheet.

2 Claims, 3 Drawing Sheets

DEVICE FOR OBTAINING STOOL SAMPLES AND DETECTING OCCULT BLOOD

This invention relates to a device for obtaining stool samples for use in testing for occult blood in the stool.

Devices which are used in the same manner as toilet tissue to obtain stool samples for testing for occult blood are disclosed in U.S. Pat. Nos. 4,259,964 to R. A. Levine; 4,273,741 to R. A. Levine; and 4,420,353 to R. A. Levine. These devices are adapted to be usable by a patient in the privacy of the home to obtain the stool sample in relatively controlled volumetric amounts. Once the sample has been gotten, the device can be hermetically sealed and returned to the physician's office for analysis. The noted devices include a stool receptor sheet which is preimpregnated with a blood detecting reagent such as guaiac. One problem associated with the use of preimpregnated guaiac sheets is that guaiac is relatively unstable when exposed to light and air and can lose its ability to detect occult blood in the stool sample. The above-noted patents do not disclose any means on the sampling device for determining whether the guaiac has or has not degraded during the time period prior to use of the device.

U.S. Pat. Nos. 4,175,923 to W. G. Friend; and 4,365,970 to P. J. Lawrence et al both disclose devices for testing stool samples for occult blood which include guaiac impregnated sheets and which also include a means for determining whether the guaiac reagent has retained its ability to detect the blood. The U.S. Pat. No. 4,175,923 discloses a sheet which is partially impregnated with blood and which is exposed to stool. A comparison is made between any color change observed in the blood impregnated portion of the sheet and observed in the part of the sheet exposed to the stool. The U.S. Pat. No. 4,365,970 to P. J. Lawrence et al discloses a stool sampling device which includes a positive performance monitor to ensure that the guaiac has not been desensitized.

In both of these prior art devices, the positive monitor is at all times in direct contact with the guaiac impregnated sheet. Thus, from manufacture to use, the positive monitor in the prior art occult blood testing devices remains in intimate contact with the guaiac. This long term intimate contact between the guaiac and the performance/control monitor is undesirable because this condition results in a heme-guaiac complex being produced, which is very stable and which will show a positive reaction color change when a developer reagent, such as peroxide, is added, even after the guaiac in the paper has lost its ability to indicate the presence of blood in the stool. Thus, the positioning of the performance/control monitor directly on the guaiac paper, when the device is manufactured, can result in a false indication that the guaiac paper is capable of functioning properly. From the foregoing, it is apparent that such a device could fail to indicate the presence of internal bleeding.

The device of this invention can be used in the same manner as toilet tissue to obtain the stool samples, includes a performance/control monitor, and will not provide false indications that the guaiac impregnated paper is viable. The device of this invention is a multilayered pliable product which includes a first impervious pliable sheet formed from a paper-plastic laminate or the like. This impervious sheet is divided in relatively equal halves by a transverse fold line. This sheet has an internal surface, which is adhesively tacky over its entirety. One of the halves of the impervious sheet is cut to form an access door which can be released from the remainder of that half of the sheet to provide an opening therein for analyzing the stool sample. The access door has a release sheet adhered thereto to prevent it from adhering to the stool receptor sheet before the stool sample is analyzed. The same half of the impervious sheet has adhered thereto the stool receptor sheet, which overlies the access door. The other one of the halves of the impervious sheet has disposed thereon a performance/control monitoring member which is used to check the viability of the guaiac on the stool receptor sheet. The other half of the impervious sheet also has a marginal closure flap which has disposed thereon a peelable release sheet to render it initially non-tacky. A cover sheet overlies both halves of the impervious sheet and is peelably removable therefrom. The cover sheet is provided with a plurality of stool access openings overlying the stool receptor sheet. The cover sheet overlies the performance/control monitoring member to protect it from air and also to separate it from the guaiac on others of the device which may be packed together in a carton or the like.

It is, therefore, an object of this invention to provide a stool sampling device which may be used in the same fashion as toilet tissue to obtain volumetric samples of stool to be tested for the presence or absence of occult blood.

It is an additional object of this invention to provide a device of the character described which includes a stool receptor sheet which is impregnated with a blood detecting reagent.

It is a further object of this invention to provide a device of the character described which includes a performance/control monitoring member which is brought into contact with the receptor sheet only after the stool sample is taken and which provides an indication of the state of the reagent in the receptor sheet.

BRIEF DESCRIPTION OF THE DRAWINGS

These and other objects and advantages of the invention will be more readily apparent from the following detailed description of a preferred embodiment thereof when taken in conjunction with the accompanying drawings, in which.

Figure 1:
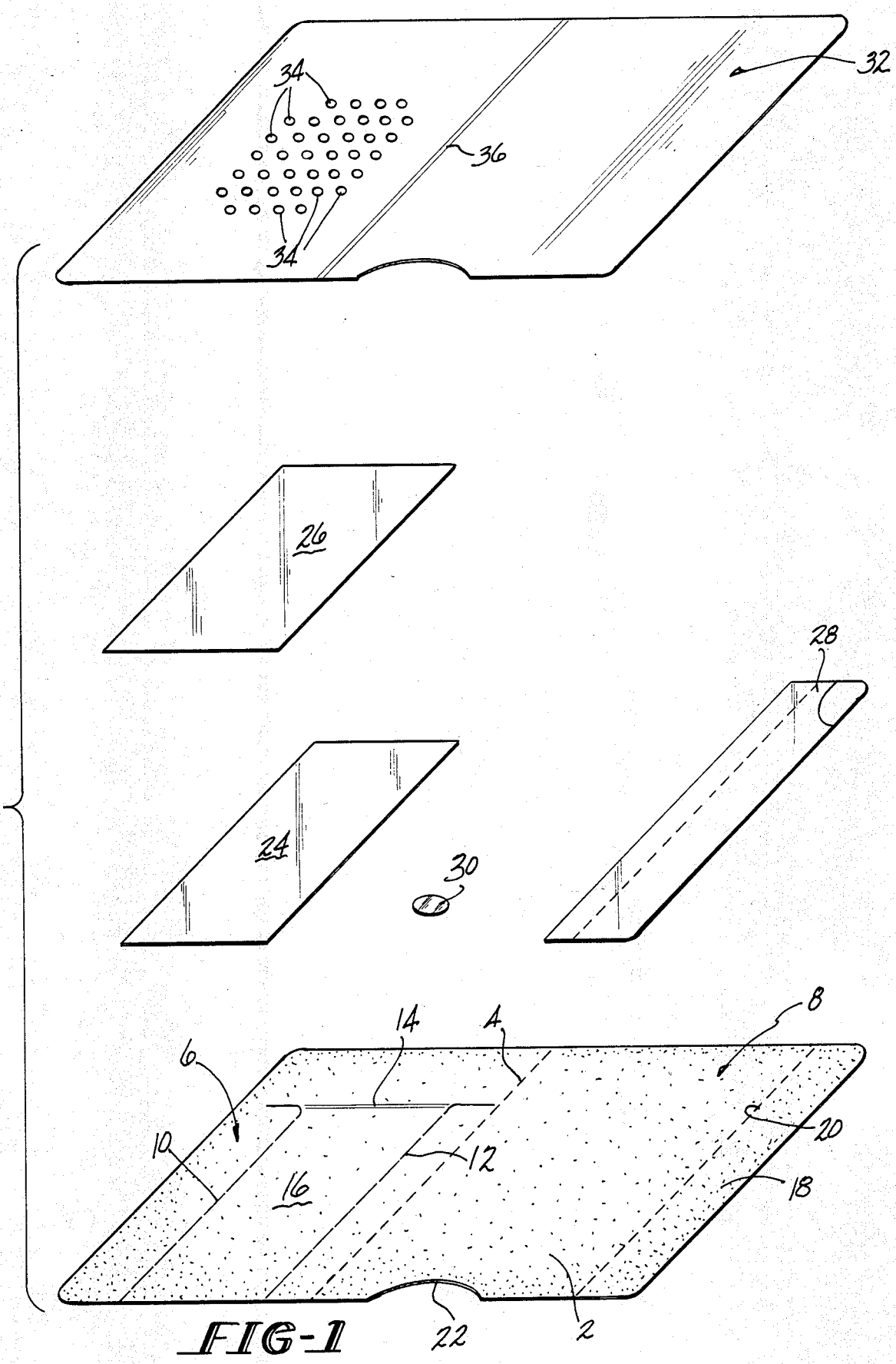
FIG. 1 is an exploded perspective view of a preferred embodiment of a stool sampling device formed in accordance with this invention.

Referring now to the drawings, there is shown in FIG. 1 a preferred embodiment of the device of this invention which includes an impervious sheet 2 which may be made from a paper-plastic laminate or the like. The sheet 2 has a fold line 4 which divides it into approximately equal halves 6 and 8. The first half 6 includes a pair of rupturable cut score lines 10 and 12 which extend from one edge of the sheet 2 to a fold line 14 to form an access door 16 in the sheet 2. The sheet 2 also includes a closure flap 18 connected to the second half 8 by a fold line 20. A notch 22 is formed in one edge of the second half 8 of the sheet 2. The entire inner surface of the sheet 2 which is shown in FIG. 1 is tacky so as to adhesively secure components of the device thereto.

A release sheet 24 is secured to the tacky surface of the access door 16 to prevent the stool receptor sheet 26 from initially adhering to the access door 16. A release sheet 28 is also secured to the sheet 2 to overlie the closure flap 18 to protect the tackiness of the latter. The performance/control monitor member 30 is also secured to the sheet 2. The member 30 is preferably cut from a sheet of paper which is impregnated with a solution of hematin, or a similar peroxidatively active material, which will mimic the presence of occult blood in the stool sample when the developing solution is applied to it. The stool receptor sheet 26 is secured to the sheet 2 in overlying relationship to the release sheet 24. The receptor sheet 26 is impregnated with a reagent, such as guaiac, which will indicate the presence of blood in the stool sample. The side edges of the receptor sheet 26 extend beyond the side edges of the release sheet 24 sufficiently so that the receptor sheet 26 will adhere to the sheet 2 along the edges of the receptor sheet 26. The receptor sheet 26 is made from a fibrous material such as an absorbant paper, or the like.

Overlying the sheets 2, 24, 26, 28 and 30 is a cover sheet 32, which is a soft pliant material such as polyethylene plastic or the like. The cover sheet has a plurality of holes 34 formed in the half thereof, which overlies the receptor sheet 26. A medial fold line 36 is aligned with the fold line 4 on the impermeable sheet 2. The cover sheet 32 is adhered to tacky exposed portions of the impermeable sheet 2 but can be pulled away therefrom after the stool sample is taken.

Figure 2:
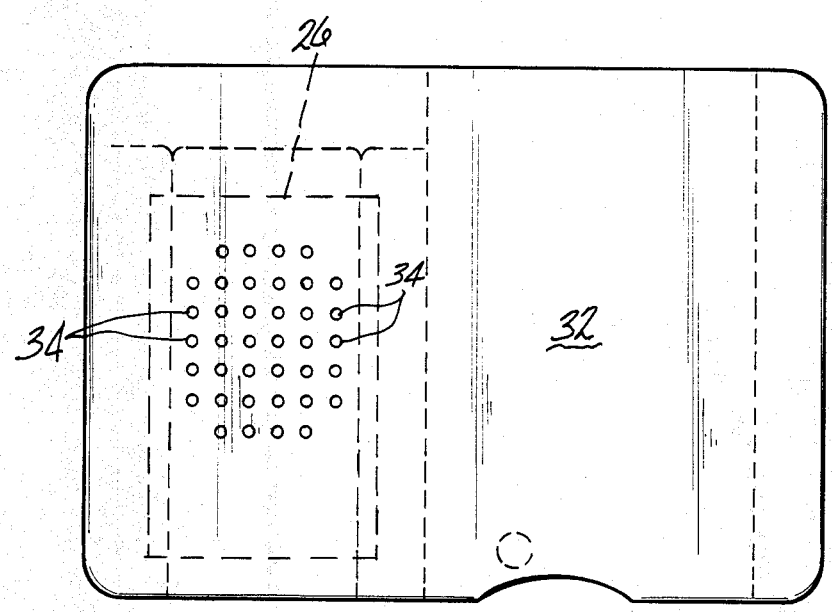
FIG. 2 is a plan view of the device of FIG. 1 showing the side of the device on which the stool is deposited.
Figure 3:
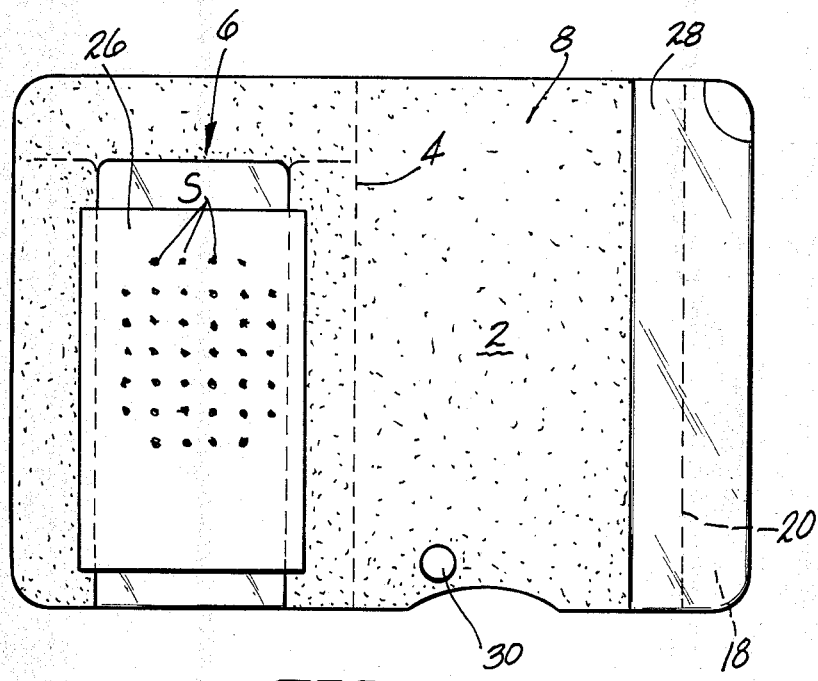
FIG. 3 is a plan view similar to FIG. 2 but showing the device after the discardable sheet has been removed from the device.
Figure 4:
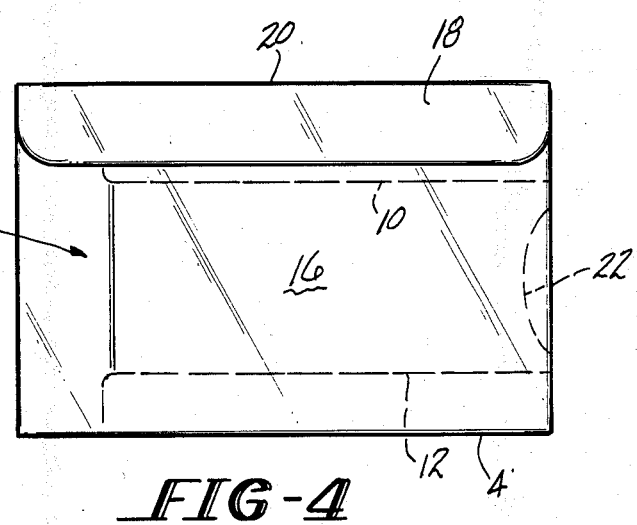
FIG. 4 is a plan view of the device after it has been folded and sealed so that the stool specimen can be returned to the physician's office for analysis.

The assembled device is shown in FIG. 2. To obtain the stool sample, after defecation, the patient draws the cover sheet 32 and its holes 34 across the rectum in the same manner as toilet tissue is used. Stool is thus wiped onto the cover sheet 32 and passes through the openings 34 to be deposited in spots on the receptor sheet 26. The cover sheet 32 is then peeled off of the remainder of the device and discarded into the toilet. The result will be the device as seen in FIG. 3, the stool spots being designated as S on the receptor sheet 26. Removal of the cover sheet 32 thus exposes the stool spots S of the receptor sheet 26, the performance/control monitor member 30, and the closure flap release sheet 28. It will be noted that the surface of the impermeable sheet 2 surrounding the control performance monitor 30 is adhesively tacky. The closure flap release sheet 28 is then peeled off of the impermeable sheet 2 to expose the closure flap 18. The stool spots S are then effectively sealed in the device by folding the impermeable sheet 2 about the fold line 4 to bring the half 8 into face-to-face contact with the half 6, the halves 6 and 8 adhering to each other due to the tackiness of the sheet 2. The performance/control monitor 30 is thus brought into face-to-face contact with the guaiac impregnated receptor sheet 26 and is held thereagainst by the tackiness of the sheet 2. The closure flap 18 is then folded about the fold line 20 and adhered to the outer surface of the half 6, as shown in FIG. 4. Thusly sealed, the device is returned to the physician's office for analysis.

Figure 5:
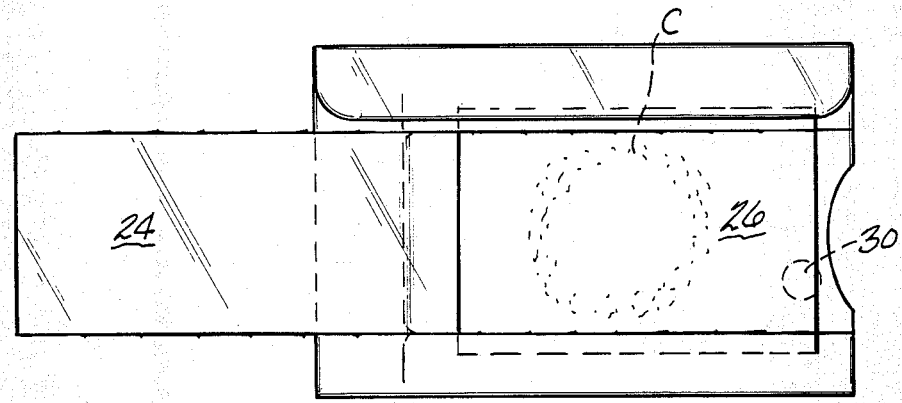
FIG. 5 is a plan view of the device after the access door has been opened to expose the stool receptor sheet for the application of the developing reagent.

The physician, upon receipt of the device, which displays patient identity information, grasps the access door 16 at the end thereof overlying the notch 22 and pulls back to rupture the cut score lines 10 and 12. The access door 16 is thus pulled back to the position shown in FIG. 5 to expose the receptor sheet 26. It will be noted that the stool spots and performance/control monitor 30 are positioned on the inner surface of the sheet 26, the spots being generally within the area bounded by the circle C shown in phantom in FIG. 5. The developing reagent is then applied to the area of the sheet 26 within the circle C and to the area of the sheet 26 overlying the performance/control monitor 30. A blue color over the control performance monitor indicates that the guaiac is valid, and blue coloring in the stool spot zone indicates the presence of blood in the stool. Absence of a blue color over the control performance monitor indicates that the guaiac is not valid and that another test should be performed.

Figure 6:
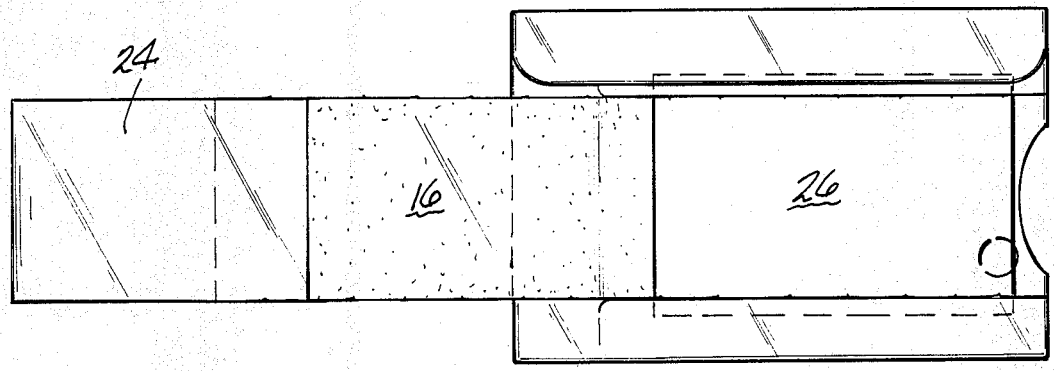
FIG. 6 is a plan view similar to FIG. 5 showing the release sheet being peeled away from the inner surface of the access door to adapt the door for adhesive securement to the stool receptor sheet to seal the device for discarding.

After the developer reagent has been applied and the results recorded, the release sheet 24 is peeled off of the access door 16, as shown in FIG. 6, thus exposing the adhesively tacky inner surface of the access door 16. The door 16 is then returned to its original position, as shown in FIG. 4, and pressed against the receptor sheet 26 to effectively seal the stool specimen in the device. The device may then be discarded with minimal chance of contamination or odor occurring.

It will be readily appreciated that the device of this invention will provide an accurate assessment of the operability of the guaiac or other reagent used on the stool receptor sheet at the time the analysis is made. By maintaining the performance/control monitor away from and out of contact with the receptor sheet until the stool sample is taken, there is no chance that the monitor can provide a false positive reading by being stabilized by the guaiac reagent. The receptor sheet and the monitor are both protected against adverse conditions by the cover sheet until the stool sample is taken and the device then sealed.

Since many changes and variations of the disclosed embodiment of the invention may be made without departing from the inventive concept, it is not intended to limit the invention otherwise than is required by the appended claims.

What is claimed is:

1. A stool sampling device in the form of a multilayered pliant product, said device comprising:
   (a) an impermeable pliant sheet divided generally into first and second halves;
   (b) means forming an access door in said first half of said impermeable sheet which is operable to create an opening therein;
   (c) a stool receptor sheet adhesively secured to said first half of said impermeable sheet and overlying said access door, said receptor sheet being impregnated with a guaiac reagent which reacts with blood constituents when subjected to an oxidizing developer reagent to cause the guaiac reagent to undergo a characteristic color change;
   (d) a performance/control monitor disposed on said second half of said impermeable sheet spaced apart from said receptor sheet, said performance/control monitor comprising a reactant which will, when it is in contact with said guaiac reagent while being subjected to an oxidizing developer reagent, react with the guaiac reagent and cause said guaiac reagent to undergo its characteristic color change, said monitor being positioned so that it will be brought into contact with said receptor sheet only when said impermeable sheet is folded so as to bring said first and second halves into face-to-face contact with each other;

(e) means associated with said impermeable sheet to hold said monitor in contact with said receptor sheet when said first and second halves of said impermeable sheet are thus brought into face-to-face contact; and (f) a cover sheet overlying said impermeable sheet, said receptor sheet, and said monitor, said cover sheet including means defining openings therein positioned so as to allow deposition of stool on said receptor sheet through said openings, and said cover sheet being peelably removable from said impermeable sheet.

2. A stool sampling device in the form of a multilayered pliant product, said device comprising:

(a) an impermeable pliant sheet having an inner surface which is adhesively tacky throughout its entirety, and which is divided by a transverse fold line into relatively equal first and second halves;

(b) means forming an access door in said first half of said impermeable sheet, said access door being operable to form an opening in said impermeable sheet;

(c) a guaiac reagent impregnated stool receptor sheet secured to said tacky inner surface of said impermeable sheet, said receptor sheet overlying said access door;

(d) a control and performance monitor adhesively secured to said tacky inner surface of said impermeable sheet on said second half thereof, said monitor containing a reactant which will, when it is in contact with said guaiac reagent while being subjected to an oxidizing developer reagent, react with said guaiac reagent to cause a color change which is characteristic of a reaction of said guaiac reagent with blood in the presence of an oxidizing developer reagent; said control and performance monitor being offset from and out of contact with said receptor sheet, and said monitor being positioned so as to be brought into face-to-face contact with said receptor sheet only when said impermeable sheet is folded about said transverse fold line, said monitor being operable to determine the activity level of said guaiac reagent in said receptor sheet; and (e) a non-tacky cover sheet overlying said impermeable sheet, said receptor sheet, and said monitor, said cover sheet being peelable away from said impermeable sheet to uncover said tacky inner surface of said impermeable sheet to allow said tacky inner surface to hold said monitor against said receptor sheet when said impermeable sheet is folded about said transverse fold line, said cover sheet having means defining openings therein positioned so as to allow deposition of stool on said receptor sheet through said openings.

* * * * *